US008425892B2

(12) United States Patent
Bologna et al.

(10) Patent No.: US 8,425,892 B2
(45) Date of Patent: Apr. 23, 2013

(54) EXTENDED, CONTROLLED-RELEASE PHARMACEUTICAL COMPOSITIONS USING CHARGED POLYMERS

(75) Inventors: William J. Bologna, Paris (FR); Howard L. Levine, Oceanside, NY (US)

(73) Assignee: Columbia Laboratories, Inc., Livingston, NJ (US)

( * ) Notice: Subject to any disclaimer, the term of this patent is extended or adjusted under 35 U.S.C. 154(b) by 787 days.

(21) Appl. No.: 10/423,920

(22) Filed: Apr. 28, 2003

(65) Prior Publication Data

US 2003/0211071 A1    Nov. 13, 2003

Related U.S. Application Data

(63) Continuation-in-part of application No. 10/278,912, filed on Oct. 24, 2002, now abandoned.

(60) Provisional application No. 60/438,501, filed on Jan. 8, 2003, provisional application No. 60/330,684, filed on Oct. 29, 2001.

(51) Int. Cl.
*A61K 31/74* (2006.01)
(52) U.S. Cl.
USPC ........................................................ 424/78.1
(58) Field of Classification Search ................ 424/486, 424/78.1
See application file for complete search history.

(56) References Cited

U.S. PATENT DOCUMENTS

| | | | |
|---|---|---|---|
| 3,427,379 A | 2/1969 | Barry et al. | 424/14 |
| 4,615,697 A | 10/1986 | Robinson | |
| 4,795,436 A | 1/1989 | Robinson | 424/422 |
| 4,795,644 A | 1/1989 | Zentner | |
| 4,983,392 A * | 1/1991 | Robinson | |
| 5,102,666 A | 4/1992 | Acharya | 424/487 |
| 5,110,605 A | 5/1992 | Acharya | 424/487 |
| 5,225,196 A | 7/1993 | Robinson | 424/427 |
| 5,234,957 A | 8/1993 | Mantelle | 514/772.6 |
| D345,211 S | 3/1994 | Bologna | D24/141 |
| 5,332,576 A | 7/1994 | Mantelle | 424/443 |
| 5,387,419 A | 2/1995 | Levy et al. | 424/422 |
| 5,446,070 A | 8/1995 | Mantelle | 514/772.6 |
| 5,472,704 A | 12/1995 | Santus et al. | 424/435 |
| 5,474,768 A | 12/1995 | Robinson | 424/78.31 |
| 5,508,045 A | 4/1996 | Harrison et al. | 424/608 |
| 5,543,150 A | 8/1996 | Bologna et al. | 424/430 |
| D375,352 S | 11/1996 | Bologna | D24/115 |
| 5,576,025 A | 11/1996 | Akiyama et al. | 424/501 |
| 5,578,315 A * | 11/1996 | Chien et al. | 424/435 |
| 5,658,956 A * | 8/1997 | Martin et al. | 514/724 |
| 5,667,492 A | 9/1997 | Bologna et al. | 604/57 |
| 5,700,485 A | 12/1997 | Berde et al. | 424/501 |
| 5,731,006 A | 3/1998 | Akiyama et al. | 424/502 |
| 5,811,126 A * | 9/1998 | Krishnamurthy | 424/498 |
| 5,876,744 A * | 3/1999 | Della Valle et al. | 424/434 |
| 5,932,248 A | 8/1999 | Chen | |
| 5,955,096 A | 9/1999 | Santos et al. | 424/434 |
| 5,968,500 A | 10/1999 | Robinson | 424/78.08 |
| 5,985,861 A | 11/1999 | Levine et al. | 514/170 |
| 5,989,535 A | 11/1999 | Nayak | 424/78.02 |
| 5,993,856 A | 11/1999 | Ragavan et al. | 424/489 |
| 6,054,447 A | 4/2000 | Levine et al. | 514/177 |
| 6,086,909 A * | 7/2000 | Harrison et al. | 424/430 |
| 6,123,965 A | 9/2000 | Jacob et al. | 424/489 |
| 6,126,959 A * | 10/2000 | Levine et al. | |
| 6,135,153 A | 10/2000 | Cleland, Sr. et al. | 137/625.46 |
| 6,159,491 A | 12/2000 | Durrani | |
| 6,180,355 B1 | 1/2001 | Alexander et al. | 435/7.1 |
| 6,197,327 B1 | 3/2001 | Harrison et al. | 424/430 |
| 6,207,696 B1 | 3/2001 | Peterson et al. | 514/400 |
| 6,238,687 B1 | 5/2001 | Mao et al. | 424/426 |
| 6,248,358 B1 | 6/2001 | Bologna et al. | 424/465 |
| 6,264,973 B1 | 7/2001 | Mahashabde et al. | 424/432 |
| 6,303,628 B1 * | 10/2001 | Nakao et al. | 514/307 |
| 6,306,914 B1 | 10/2001 | de Ziegler et al. | 514/899 |
| 6,319,513 B1 * | 11/2001 | Dobrozsi | 424/434 |
| 6,358,525 B1 | 3/2002 | Guo et al. | 424/464 |
| 6,368,586 B1 | 4/2002 | Jacob et al. | 424/78.08 |
| 6,368,635 B1 | 4/2002 | Akiyama et al. | 424/501 |
| 6,403,640 B1 | 6/2002 | Stoner et al. | 514/473 |
| 6,479,045 B2 * | 11/2002 | Bologna et al. | |

(Continued)

FOREIGN PATENT DOCUMENTS

EP    0 147 780 A    7/1985
EP    1 210 934    6/2002

(Continued)

OTHER PUBLICATIONS

Voorspoels, J. et al., "Buccal Absorption of Testosterone and Its Esters Using a Bioadhesive Tablet in Dogs," Pharmaceutical Research, vol. 13, No. 8, 1996, pp. 1228-1232.
Park, H., Robinson J.R. Physico-chemical properties of water insoluble polymers important to mucin/epithelial adhesion. J Controlled Release 1985; 2:45-57.
Robinson, J.R., Leung, S-H.S., Park, H. Mechanisms of adhesion of swelling insoluble polymers to mucin-epithelial surfaces. Proceedings of the 12th International Symposium on Controlled Release of Bioactive Materials; Jul. 8-12, 1985; Geneva, Switzerland.
March, C., Nakamura, R. Evaluation of the duration of effect of a bioadhesive vaginal moisturing gel on vaginal pH. Presented at the 7th International Congress on the Menopause; Jun. 20-24, 1993, Stockholm, Sweden. Abstract.
Bures et al (Surface Modifications and Molecule imprinting of polymers in medical and pharmaceutical applications. J Control Release May 14, 2001;72(1-3):25-33).
Duncan et al (Biological Effects of Soluble Synthetic Polymers as Drug Carriers, Crit Rev Ther Drug Carrier Syst. 1985;1(4):281-310).
Guo and Cremer, 1999. Development of Bioadhesive Buccal Patches. In Mathiowitz, Edith (Ed.) Bioadhesive Drug Delivery Systems, (pp. 541-562) New York: Marcel Dekker, Inc.).

(Continued)

*Primary Examiner* — Jake M. Vu
(74) *Attorney, Agent, or Firm* — Winston & Strawn LLP (57) ABSTRACT

The present invention relates to a delivery system for pharmaceutical compositions relying in part on an ionic interaction to control and facilitate release of the treating agent. More specifically, the invention relates to an extended controlled-release system having an ionic treating agent and an ionic polymer, wherein the polymer is sufficiently ionized to release the treating agent in a controlled manner over an extended period of time and the composition does not require an emulsion system for administering the treating agent.

38 Claims, 3 Drawing Sheets

U.S. PATENT DOCUMENTS

| | | | |
|---|---|---|---|
| 6,486,207 | B2 | 11/2002 | Yeager et al. .................. 514/573 |
| 6,509,028 | B2 | 1/2003 | Williams et al. ............... 424/434 |
| 6,585,997 | B2 * | 7/2003 | Moro et al. ..................... 424/434 |
| 2002/0012674 | A1 | 1/2002 | Saettone et al. |
| 2002/0044964 | A1 | 4/2002 | Bologna et al. ............... 424/465 |
| 2002/0045668 | A1 | 4/2002 | Dang et al. |
| 2003/0091644 | A1 | 5/2003 | Bologna et al. ............... 424/486 |

FOREIGN PATENT DOCUMENTS

| | | | |
|---|---|---|---|
| FR | 2 720 276 | A | 12/1995 |
| RU | 2100367 | C1 | 12/1997 |
| UA | 45379 | | 4/2002 |
| WO | WO 91/06290 | A1 | 5/1991 |
| WO | WO 93/00058 | A | 1/1993 |
| WO | WO 95/07699 | A1 | 3/1995 |
| WO | WO 95/15137 | | 8/1995 |
| WO | WO 96/10989 | A1 | 4/1996 |
| WO | WO 97/44032 | | 11/1997 |
| WO | WO 98/23292 | A | 6/1998 |
| WO | WO 98/35676 | | 8/1998 |
| WO | WO 98/56323 | A1 | 12/1998 |
| WO | WO 99/13862 | A2 | 3/1999 |
| WO | WO 99/15210 | A2 | 4/1999 |
| WO | WO 99/55334 | A1 | 11/1999 |
| WO | WO 00/10536 | | 3/2000 |
| WO | WO 00/78298 | | 12/2000 |
| WO | WO 01/15687 | A1 | 3/2001 |
| WO | WO 01/24788 | | 4/2001 |
| WO | WO 01/95888 | | 12/2001 |
| WO | WO 02/051382 | | 7/2002 |

OTHER PUBLICATIONS

Glantz et al (Bioadhesion-a phenomenon with multiple dimensions. Acta Odontol Scand. Oct. 1999;57(5):238-41).

Lee et al (Bioadhesive-Based Dosage Forms: The Next Generation. Journal of Pharmaceutical Sciences 2000; 89(7);850-866).

Peppas et al (Hydrogels as mucoadhesive and bioadhesive materials: a review. Biomaterials 1996; 17(16):1553-1561).

Prestrelski et al (Dehydration-induced Conformation Transitional in Proteins and Their Inhibition by Stabilizers, Biophysical Journal 1993. 65:661-671).

Robinson et al (Bioadhesive Polymers for Controlled Drug Delivery, Ann N Y Acad Sci. 1987;507:307-14).

John Smart, 1999. The role of water movement and Polymer Hydration in Mucoadhesion. In Mathiowitz, Edith (Ed.) Bioadhesive Drug Delivery Systems, (pp. 11-23) New York: Marcel Dekker, Inc.

Andersch, B., et al., "An Epidemiologic Study of Young Women with Dysmenorrhea," *American Journal of Obstetrics and Gynecology*, vol. 144, No. 6, (Nov. 15, 1982), 655-660.

Forman, A., et al., "Aspects of Inhibition of Myometrial Hyperactivity in Primary Dysmenorrhea," *Acta Obstetricia et Gynecologica Scandinavica*, Suppl. 113, (1983), 71-76.

Hunter, R.H.F., et al., "Regulation of Oviduct Function in Pigs by Local Transfer of Ovarian Steroids and Prostaglandins: A Mechanism to Influence Sperm Transport," *European Journal of Obstetrics, Gynecology and Reproductive Biology*, vol. 14, (1983), 225-232.

Abstract, Derwent Publications Ltd., An 84-071329, '12!, XP002096704, AB J59025320, Feb. 9, 1984.

Caritis, S., et al., "A Double-Blind Study Comparing Ritodrine and Terbutaline in the Treatment of Preterm Labor," *American Journal of Obstetrics and Gynecology*, vol. 150, No. 1, (Sep. 1, 1984), 7-14.

Bengtsson, B., "Plasma Concentration and Side-Effects of Terbutaline," *European Journal of Respiratory Diseases*, (1984) 65, Suppl. 134, 231-235.

Berg, G., et al., "Terbutaline in the Treatment of Preterm Labour," *European Journal of Respiratory Diseases*, (1984) 65, Suppl. 134, 219-230.

Bergman, B., et al., "Transfer of Terbutaline Across the Human Placenta in Late Pregnancy," *European Journal of Respiratory Diseases*, (1984) 65, Suppl. 134, 81-86.

Nyberg, L., "Pharmacokinetic Parameters of Terbutaline in Healthy Man. An Overview," *European Journal of Respiratory Diseases*, (1984) 65, Suppl. 134, 149-160.

Ripe, E., et al., "Oral Administration of Terbutaline in Asthmatic Patients," *European Journal of Respiratory Diseases*, (1984) 65, Suppl. 134, 171-179.

Van den Berg, W., et al., "The Effects of Oral and Subcutaneous Administration of Terbutaline in Asthmatic Patients," *European Journal of Respiratory Diseases*, (1984) 65, Suppl. 134, 181-193.

Kullander, S., et al., "On Resorption and the Effects of Vaginally Administered Terbutaline in Women with Premature Labor," *Acta Obstetricia et Gynecologica Scandinavica*, vol. 64, No. 7, (1985), 613-616.

Bulletti, C., et al., "Extracorporeal Perfusion of the Human Uterus," *American Journal of Obstetrics and Gynecology*, vol. 154, No. 3, (Mar. 1986), 683-688.

Bulletti, C., et al., "A 48-Hour Preservation of an Isolated Human Uterus: Endometrial Responses to Sex Steroids," *Fertility and Sterility*, vol. 47, No. 1, (Jan. 1987), 122-129.

Bulletti, C., et al., "Extraction of Estrogens by Human Perfused Uterus," *American Journal of Obstetrics and Gynecology*, vol. 159, No. 2, (Aug. 1988), 509-151.

Kopelman, J.N., et al., "Randomized Comparison of Oral Terbutaline and Ritodrine for Preventing Recurrent Preterm Labor," *Journal of Reproductive Medicine*, vol. 34, No. 3, (Mar. 1989), 225-230.

Morgan, D.J., "Clinical Pharmacokinetics of β-Agonists," *Clinical Pharmacokinetics*, vol. 18, No. 4, (Apr. 1990), 270-294.

Krzymowski, T., et al., "Uterine and Ovarian Countercurrent Pathways in the Control of Ovarian Function in the Pig," *Journals of Reproduction and Fertility*, Suppl. 40, (1990), 179-191.

Robinson, J.C., et al., "Dysmenorrhea and Use of Oral Contraceptives in Adolescent Women Attending a Family Planning Clinic," *American Journal of Obstetrics and Gynecology.*, vol. 166, No. 2, (Feb. 1992), 578-583.

The Canadian Preterm Labor Investigators Group, "Treatment of Preterm Labor with the Beta-Adrenergic Agonist Ritodrine," *The New England Journal of Medicine*, vol. 327, No. 5, (Jul. 30, 1992), 308-312.

Einer-Jensen, N., "Counter Current Transfer Between Blood Vessels in the Ovarian Adnex," Summary of Doctoral Thesis, *Acta Obstetricia et Gynecologica Scandinavica*, (1992), vol. 71:566-567.

Creasy, R.K., et al., "Basic Research and Clinical Experience with β-Adrenergic Tocolytics in the United States," *Preterm Birth*, 2d Ed., McGraw-Hill, Inc., (1993), 243-277.

Einer-Jensen, N., et al., "Rapid Absorption and Local Redistribution of Progesterone after Vaginal Application in Gilts," *Acta Veterinaria Scandinavica*, vol. 34, No. 1, (1993), 1-7.

Fuchs, F., et al., "Principles of Tocolysis: An Overview," *Preterm Birth*, 2d Ed., McGraw-Hill, Inc., (1993), 217-227.

Miles, R.A., et al., "Pharmacokinetics and Endometrial Tissue Levels of Progesterone after Administration by Intramuscular and Vaginal Routes: A Comparative Study," *Fertility and Sterility*, vol. 62, No. 3, (Sep. 1994), 485-490.

McCombs, J., "Update on Tocolytic Therapy," *The Annals of Pharmacotherapy*, vol. 29, No. 5, (May 1995), 515-522.

Lockwood, C.J., "The Diagnosis of Preterm Labor and the Prediction of Preterm Delivery," *Clinical Obstetrics and Gynecology*, vol. 38, No. 4, (Dec. 1995), 675-687.

de Ziegler, D., et al., "Transvaginal Administration of Progesterone: The Vaginal Paradox and the First Uterine Pass Effect Hypothesis," *References en Gynecologie Obstetrique*, vol. 3, No. 3, (1995), 267-272.

Casanas-Roux, F., et al., "Morphometric, Immunohistological and Three-Dimensional Evaluation of the Endometrium of Menopausal Women Treated by Oestrogen and Crinone, A New Slow-Release Vaginal Progesterone," *Human Reproduction*, vol. 11, No. 2, (Feb. 1996), 357-363.

Harlow, S.B., "A Longitudinal Study or Risk Factors for the Occurrence, Duration and Severity of Menstrual Cramps in a Cohort of College Women," *British Journal of Obstetrics and Gynaecology*, vol. 103, (Nov. 1996), 1134-1142.

Hadfield, R., et al., "Delay in the Diagnosis of Endometriosis: A Survey of Women from the USA and the UK," *Human Reproduction*, vol. 11, No. 4, (1996), 878-880.

*Physician's Desk Reference*, 50 Ed., pp. 1502-1503 (1996).

Fanchin, R., et al., "Transvaginal Administration of Progesterone," *Obstetrics & Gynecology*, vol. 90, No. 3, (Sep. 1997), 396-401.

Bulletti, C., et al., "Targeted Drug Delivery in Gynaecology: The First Uterine Pass Effect," *Human Reproduction*, vol. 12, No. 5, (1997), 1073-1079.

Hansen, M.K., et al., "Beta-Receptor Stimulation in Essential Dysmenorrhea," *American Journal of Obstetrics and Gynecology*, vol. 121, No. 4, (Feb. 15, 1975), 566-567.

Akerlund, M., et al., "Effects of Terbutaline on Human Myometrial Activity and Endometrial Blood Flow," *Obstetrics and Gynecology*, vol. 47, No. 5, (May 1976), 529-535.

Salamanca, A., et al., "Subendometrial Contractility in Menstrual Phase Visualized by Transvaginal Sonography in Patients with Endometriosis," *Fertility and Sterility*, vol. 64, No. 1, (Jul. 1995), 193-195.

Boyle, J., "Beta-Adrenergic Agonists," *Clinical Obstetrics and Gynecology*, vol. 38, No. 4, (Dec. 1995), 688-696.

Akerlund, M., et al., "Effects of Terbutaline on Myometrial Activity, Uterine Blood Flow, and Lower Abdominal Pain in Women with Primary Dysmenorrhea," *British Journal of Obstetrics and Gynaecology*, vol. 83, No. 9, (Sep. 1976), 673-678.

Hörnblad, Y., et al., "The Metabolism and Clinical Activity of Terbutaline and its Prodrug Ibuterol," *European Journal of Clinical Pharmacology*, vol. 10, No. 1, (1976), 9-18.

Caritis, S., et al., "Effects of Terbutaline on the Pregnant Baboon and Fetus," *Obstetrics and Gynecology*, vol. 50, No. 1, (Jul. 1977), 56-60.

Caritis, S., et al., "Effects of Terbutaline on Cardiovascular State and Uterine Blood Flow in Pregnant Ewes," *Obstetrics and Gynecology*, vol. 50, No. 5, (Nov. 1977), 603-606.

Akerlund, M., et al., "Relief of Pain in Primary Dysmenorrhea by β-Adrenoceptor Stimulating Drugs," (Letter to the Editor), *Acta Obstetricia et Gynecologica Scandinavica*, 56:255-256 (1977).

Klein, J., et al., "Epidemiology of Adolescent Dysmenorrhea," *Pediatrics*, vol. 68, No. 5, (Nov. 1981), 661-664.

Kullander, S., et al., "Terbutaline Inhalation for Alleviation of Severe Pain in Essential Dysmenorrhea," *Acta Obstetricia et Gynecologica Scandinavica*, vol. 60, No. 4, (1981), 425-427.

Lalos, O., et al., "Effect of Salbutamol on the Non-Pregnant Human Uterus in Vivo," *Acta Obstetricia et Gynecologica Scandinavica*, vol. 60, No. 4, (1981), 349-352.

A. Davies et al., "Lignocaine aerosol spray in outpatient hysteroscopy: a randomized double-blind placebo-controlled trial," *Fertil Steril*, vol. 67, No. 6, 1019-1023 (1997).

A. Duleba et al., "Evaluation and Management of Chronic Pelvic Pain," *J Am Assoc Gynecol Laparoscs*, vol. 3, No. 2, 205-227 (1996).

U. Ezeh et al., "Local anaesthetic on Filshie clips for pain relief after tubal sterilisation: a randomised double-blind controlled trial," *Lancet*, vol. 346, 82-85 (1995).

F. Ling et al., "Use of Trigger Point Injections in Chronic Pelvic Pain," *Obstet Gynecol Clin North Am*, vol. 20, No. 4, 809-815 (1993).

B. Sandahl et al., "Local Application of Ketocaine for Treatment of Referred Pain in Primary Dysmenorrhea," *Acta Obstet Gynecol Scand*, vol. 59, No. 3, 259-260 (1980).

J. Slocumb, "Neurological factors in chronic pelvic pain: Trigger points and the abdominal pelvic pain syndrome," *Am J Obstet Gynecol*, vol. 149, No. 5, 536-543 (1984).

M. Trolice et al., "Anesthetic Efficacy of Intrauterine Lidocaine for Endometrial Biopsy: A Randomized Double-Masked Trial," *Obstet Gynecol*, vol. 95, No. 3, 345-347 (2000).

U. Wesselmann, "Pelvic Pain: A Chronic Visceral Pain Syndrome", *Curr Pain Headache Rep*, vol. 5, No. 1, 13-19 (2001).

Rodriguez, I.C., Cerezo, A., and Salem, I.I., "Sistemas de liberacion Bioadhesivos", Ars Pharmaceutica, 41(1):115-128 (2000).

Willdeck-Lund et al., "The Effect of Local Anaesthetic Agents on Contractility of Human Myometrium in Late Pregnancy," Acta. Anaesth. Scand., 1979, 78-88, vol. 23(1).

Munson et al. "Lidocaine, Monoethylglycinexylidide, and Isolated Human Uterine Muscle," Anesthesiology, 1978, 183-186, vol. 48(3).

Munden, J., ed., Disease Management for Nurse Practitioners, 2001, p. 517, Lippincott, Williams & Wilkins, Springhouse, PA.

Pulkkinen, M., "Nimesulide in dysmenorrhoea," Drugs, 1993, 129-133, vol. 46, suppl. 1.

European Search Report, EP03727364.6, mailed Mar. 13, 2012.

\* cited by examiner

EXTENDED, CONTROLLED-RELEASE PHARMACEUTICAL COMPOSITIONS USING CHARGED POLYMERS

CROSS-REFERENCE TO RELATED APPLICATIONS

This application claims the benefit of U.S. Provisional Application No. 60/438,501, filed Jan. 8, 2003, and is a continuation-in-part of U.S. application Ser. No. 10/278,912, filed Oct. 24, 2002 now abandoned, which claims the benefit of U.S. Provisional Application No. 60/330,684, filed Oct. 29, 2001. The content of each of these applications is expressly incorporated herein by reference thereto.

FIELD OF INVENTION

The present invention relates to a delivery system for pharmaceutical compositions relying in part on ionic interaction to control and facilitate release of the treating agent. More specifically, the invention relates to an extended controlled-release system free of an oil phase having an ionic treating agent and an ionic polymer.

The invention also relates to a method of treating or preventing a disease or condition in a mammal using the new compositions. Furthermore, this invention also relates to a pharmaceutical composition for treating or preventing pelvic pain associated with uterine dysrhythmia, as well as to a method for treating or preventing such pain. The composition and method focus in part on local, topical use of treating agents for absorption into local tissue to prevent or treat the underlying abnormal or undesirable muscle contractions that are causing the pain or discomfort rather than merely relieving or masking the resulting pain or discomfort without affecting the cause. The invention also relates to a pharmaceutical composition for treating or improving infertility associated with uterine dysrhythmia, as well as to a method for treating or improving such infertility.

BACKGROUND OF THE INVENTION

As used herein, "sustained release" of a treating agent means that the treating agent is released over a period of time, e.g., over 6 hours or 24 hours or 72 hours, rather than almost immediately. "Controlled release" is a different issue. A drug could be released over 72 hours, but hour-to-hour variation in the rate of release could be random, for example, 600% or more. Such a formulation would be characterized as sustained but not controlled (unless the particular pattern of release was by design, and not random). The objective, which is met by using an emulsion system, is not only to sustain the effect but also to control it—to provide a rate of release in a controlled manner, often a steady rate of release, but optionally with predetermined, purposeful changes in the release rate over time. The result is a sustained, controlled release.

In previous formulations, polycarbophil and similar polymers have been utilized to sustain the action of drugs using an emulsion system to control their release. In the case of terbutaline sulfate and progesterone, the controlled, sustained release is provided by use of an emulsion system. We previously demonstrated controlled, apparent-zero-order release, i.e., a constant quantity of drug is released per unit of time, for these formulations. The previous compositions, however, all included an oil phase using an emulsion system.

Examples of our prior formulations having an oil phase and water phase include the following: the terbutaline formulations as disclosed in U.S. Pat. No. 6,126,959 and U.S. patent application Ser. No. 09/510,527; and progesterone or progestin formulations as disclosed in U.S. Pat. Nos. 5,543,150; 5,985,861; 6,054,447; 6,306,914; and 6,593,317.

Specific examples of these formulations, containing both an oil and water phase follow.

| The progesterone formula is: | |
|---|---|
| Carbopol (carbomer) 974P | 1.00% |
| NOVEON ® AA1 (polycarbophil) | 2.00% |
| Glycerin | 12.90% |
| Vestran (Light liquid paraffin) | 4.20% |
| Myverol | 1.00% |
| Sorbic Acid | 0.08% |
| Progesterone | 8.00% |
| Water | 70.82% |
| The terbutaline formula is: | |
| Terbutaline sulfate | 0.40% |
| Carbopol 974P | 3.00% |
| Polycarbophil | 2.00% |
| Glycerin | 12.90% |
| Light liquid paraffin | 4.20% |
| Polyglycosyl glycerides (Labrafil) | 1.00% |
| Methyl paraben | 0.18% |
| Sorbic Acid | 0.08% |
| Water | 76.24% |

Other patents and applications that disclose polycarbophil formulations having a treating agent that use both oil and water phases include, U.S. Pat. Nos. 4,615,697; 4,795,436; 4,983,392; 5,225,196; 5,474,768; 5,667,492; and 5,968,500; and U.S. application Ser. Nos. 09/593,603 and 10/089,796.

U.S. patent application Ser. No. 09/877,218 discloses several terbutaline formulations that do not contain an oil phase. In that application, terbutaline is in the wet granulate form, which is subsequently dried. The polymers are only mixed in after the granulate has been dried. Thus, the terbutaline formulation does not hydrate and form a complex between the polymer and the treating agent as in the present invention. Accordingly, these terbutaline formulations provide sustained, controlled release of the treating agent via a different mechanism then the present invention.

Polyacrylic acid polymers have been used to form insoluble complexes for other purposes in the past. For example, U.S. Pat. No. 3,427,379 discloses that dextromethorphan HCl can be complexed with a polyacrylic acid polymer, specifically carbomer 934P, to overcome its unpleasant bitter taste, as insoluble drugs have no taste. In this case, the complex is created in a tasteless pharmaceutical formulation, such as a suspension, that is then swallowed. As soon as the product is swallowed and reaches the acidic environment of the stomach the polyacrylic acid polymer is re-protonated and all of the dextromethorphan is made available to be absorbed immediately. The sole purpose of the invention of the '379 patent is to mask the bitter taste; it does not sustain or control the release of dextromethorphan.

Progesterone is partially soluble in the oil and water phases with the majority in suspension, creating a controlled-release system. In this example, progesterone is stored in the lipophilic fraction and suspended in the gel, thereby creating a reservoir for prolonged release. A small quantity of progesterone is also dissolved in the aqueous phase. From vaginal application, as well as all other routes of administration, only the drug in the aqueous fraction is available for diffusion into the uterus or absorption into the bloodstream. Therefore, for example, progesterone absorption from progesterone gel is not dependent on the presence of adequate local hydration because the progesterone dissolved in the aqueous phase is immediately available. Specifically, progesterone absorption from progesterone gel does not depend on the highly variable degree of vaginal secretions, as is the case for oil-based progesterone products and other non-hydrated formulations.

In an emulsion system the oil and aqueous phases are in dynamic equilibrium. For example, as progesterone diffuses into tissue or blood from the aqueous phase, it is replaced by the progesterone that is stored in the oil phase or suspension reservoir, thus, ensuring a constant and controlled release of progesterone. The polycarbophil based bioadhesive delivery system in progesterone gel ensures a sustained release of progesterone. See FIG. 1A. In these formulations the emulsion system provides the controlled release of the drug, not the polycarbophil.

Several pharmaceutical compositions have been made in an attempt to treat pelvic pain with limited success. Pelvic pain may be intermittent or recurrent, or it may be constant and severe, but it is frequently associated with uterine dysrhythmia—abnormal, disordered, or disturbed contractions of the uterus. Pelvic pain is often experienced during menses, as painful menstruation, or dysmenorrhea. Women with chronic pelvic pain associated with menstruation frequently spend one day each month in bed and also may have an additional day each month of reduced activity because of the severity of the pain. Pelvic pain may also be caused by pelvic infections, and diseases of the urinary tract or bowel.

Infertility also may be associated with uterine dysrhythmic conditions, including dysmenorrhea. See, e.g., U.S. patent application Ser. No. 10/089,796. Uterine dysrhythmias may affect the rapid transport of sperm, thus affecting fertility. Contractility along the female tract (uterus and fallopian tubes) appears to be the primary motor assuring rapid transport of sperm from the cervical area to the distal end of the tubes, where fertilization takes place. Retrograde uterine contractility appears to impede this normal transport mechanism.

Chronic pelvic pain is common in women in the reproductive age group. It causes disability and distress, and results in significant costs to health services. Overall, a woman has about a 5% risk of having chronic pelvic pain for some period of time in her lifetime. In patients with a previous diagnosis of pelvic inflammatory disease this risk is increased fourfold to approximately 20%. Recent epidemiologic data from the United States showed that 14.7% of women in their reproductive ages reported chronic pelvic pain. A total of 15% of these women with chronic pelvic pain reported time lost from work and 45% reported reduced work productivity. In the United States 10% of outpatient gynecologic consultations are for chronic pelvic pain and 40% of laparoscopies are done for chronic pelvic pain.

The pathogenesis of chronic pelvic pain is poorly understood. Often, investigation by laparoscopy may reveal endometriosis, mild to moderate, or it may reveal no obvious cause for pain. There are several possible explanations for chronic pelvic pain including undetected irritable bowel syndrome, the vascular hypothesis where pain is thought to arise from dilated pelvic veins in which blood flow is markedly reduced and altered spinal cord and brain processing of stimuli in women with chronic pelvic pain. As the pathophysiology of chronic pelvic pain is not well understood, its treatment is often unsatisfactory and limited to symptom relief. Currently, the main approaches to treatment include symptomatic treatment of pain with medication, surgery, or possibly psychotherapy and counseling.

Very little is known about effective pharmacologic treatment for chronic pelvic pain, despite the fact that it is a very common chronic pain syndrome. Several different pharmacologic classes of medications have been used to alleviate the symptomatic pain and discomfort, rather than treat or prevent the underlying cause, in patients with chronic pain syndromes: nonsteroidal anti-inflammatory drugs, anticonvulsants, local anesthetics, and opioids. Very few studies have focused on the actual treatment or prevention of the underlying cause—uterine dyskinetic contractions—in order to treat or prevent chronic pelvic pain.

Dysmenorrhea is associated with pain typically related to the menstrual cycle and can be primary or secondary. Most women experience primary dysmenorrhea at some time during their life. The pain is cramping or sharp and lasts the first few days of the menstrual period. It may radiate to the back, thighs, or deep pelvis. Occasionally, nausea or vomiting occurs. Secondary dysmenorrhea may be due to endometriosis or cervical stenosis or, if associated with heavy menstrual flow, to fibroids, adenomyosis, or large endometrial polyps.

In order to provide local or regional blockade for extended periods, clinicians currently use local anesthetics administered through a catheter or syringe to a site where the pain is to be blocked. This requires repeated administration where the pain is to be blocked over a period of greater than one day, either as a bolus or through an indwelling catheter connected to an infusion pump. These methods have the disadvantage of potentially causing irreversible damage to nerves or surrounding tissues due to fluctuations in concentration and high levels of anesthetic. In addition, anesthetic administered by these methods are generally neither confined to the target area, nor delivered in a linear, continuous manner. In all cases, analgesia rarely lasts for longer than six to twelve hours, more typically four to six hours. In the case of a pump, the infusion lines are difficult to position and secure, the patient has limited, encumbered mobility and, when the patient is a small child or mentally impaired, may accidentally disengage the pump.

U.S. Pat. No. 5,700,485 discloses a method and device for administering a local anesthetic combined with a biodegradable polymer incorporated into microspheres. Prolonged release of the anesthetic is obtained by administration with glucocorticoid.

Because high systemic anesthetic concentration can cause irritation or burning to the vagina, as well as other detrimental side effects, there is a need to keep systemic circulation of the anesthesia low. Thus, there is a need for a formulation in which local anesthetics would diffuse preferentially into the cervix for a prolonged period of time to ensure sufficient anesthesia for treating pelvic pain due to dysrhythmic conditions, while keeping systemic circulation low.

Similarly, high systemic levels of other anti-dysrhythmic treating agents may lead to adverse side effects, some of which may be severe. Many classic anti-arrhythmic (and other anti-dysrhythmic) agents themselves have the ability to cause coronary arrhythmia. Other detrimental side effects include without limitation nausea, blurred or yellow vision, precipitation of glaucoma, constipation, seizures, tremor, bone marrow aplasia, pulmonary fibrosis, hypotension, reduction of exercise heart rate, diarrhea and diarrhea-induced hypokalemia, and immunological reactions such as thrombocytopenia, hepatitis, or bone marrow depression. Thus, use of an anti-dysrhythmic agent to treat or prevent uterine dysrhythmia must carefully avoid systemic levels that could prompt coronary problems or other adverse side effects.

Accordingly, there is a need for a formulation that would locally and preferentially deliver anti-dysrhythmic treating agents to treat or prevent pelvic pain due to dysrhythmia, or to treat or improve infertility associated with dysrhythmia. The formulation should avoid blood levels of the treating agent high enough to cause detrimental side effects, while attaining sufficient local tissue levels of the treating agent to provide the desired therapeutic anti-dysrhythmic effect.

SUMMARY OF THE INVENTION

The invention relates to a bioadhesive pharmaceutical composition comprising an ionic treating agent and an ionic polymer. The composition does not rely on an emulsion system and the polymer is sufficiently ionized to provide bonding with the treating agent to release the treating agent in a controlled manner over an extended period of time. In a preferred embodiment the ionic polymer comprises a bioadhesive, water swellable, but water-insoluble cross-linked polycarboxylic acid polymer, such as polycarbophil. In another embodiment, the treating agent is anionic and is complexed with a cationic complexing agent, wherein an anionic polymer can be used. In these compositions the treating agent is typically released over a period of at least about 6 hours, preferably at least about 12 hours, more preferably at least about 24 hours, and still more preferably over a period of about two to three days. In a particular embodiment, the treating agent is released over a period of about 3.5 days. The compositions of the invention are generally in the form of a gel or a tablet, but other delivery forms are also encompassed by the invention.

In one specific embodiment of the invention, the pharmaceutical composition is formulated for treating or preventing pelvic pain, or for treating or improving infertility associated with uterine dysrhythmia. In this embodiment the composition comprises a therapeutically effective amount of an ionic, anti-dysrhythmic treating agent and a bioadhesive, water swell able, but water-insoluble cross-linked polycarboxylic acid polymer, wherein the composition does not require an emulsion system and the treating agent is released in a controlled manner over an extended period of time through chemical bonding with the polymer, wherein the polymer is sufficiently ionized to provide bonding with the treating agent.

The invention further relates to a method of treating or preventing a disease or condition in a mammal using the disclosed compositions. In a particular embodiment the disease or condition being treated is pelvic pain. In another embodiment the method is used to treat or improve infertility. In one embodiment, the treating agent is released over a period of at least one day after administration.

DETAILED DESCRIPTION OF THE INVENTION

The present invention relates to a bioadhesive pharmaceutical composition free of an oil phase. The bioadhesive composition includes an ionic polymer and an ionic treating agent. The ionic polymer is generally sufficiently ionized to allow bonding with the treating agent to release the treating agent in a controlled manner over an extended period of time.

The ionic polymer can be anionic or cationic. Typically, when a cationic polymer is used the composition further comprises a bioadhesive agent. Examples of bioadhesive agents include carbomers—high molecular weight, cross-linked acrylic acid polymers. Carbopol® 934, 940, 974, and 980 are specific examples of such carbomers.

In a nonlimiting exemplary formulation of the invention, the polymer is a bioadhesive, water swellable, but water-insoluble cross-linked polycarboxylic acid polymer. A specific example of such a polymer is polycarbophil. Polycarbophil has been used to mimic mucin, which is negatively charged, the glycoprotein component of mucus that is responsible for its attachment to underlying epithelial surfaces. Polycarbophil is a lightly cross-linked polymer. Polycarbophil is also a weak polyacid containing multiple carboxyl radicals ($COO^-$)—the source of its negative charges. These acid radicals permit hydrogen bonding with the cell surface. Hydrogen bonds are weak, but when they are numerous, for example as in polycarbophil, there is a sufficiently strong affinity to hydrogen atoms on the cell surface to adhere for an extended period of time. A negatively charged polymer exhibits a strong affinity to hydrogen atoms on the cell surface. A water-insoluble polymer, like polycarbophil, stays attached to mucosal epithelial cells often until they turn over, normally up to 3 to 5 days. The negatively charged polymer bonds to the cell surface by hydrogen bonding resulting in bioadhesion of the pharmaceutical composition.

The present invention is generally useful with any ionic treating agent. Typically, an anionic treating agent binds to a cationic polymer, while a cationic treating agents typically binds to an anionic polymer. In one embodiment of the invention, however, an anionic treating agent is used with an anionic polymer. In such an embodiment, the composition also includes a complexing agent with an available cationic moiety after combining with the treating agent, which could be a separate molecule or simply a constituent attached to the complexing agent. The cationic moiety is available to attach to the anionic polymer. However, the complexing agent does not prevent the treating agent from being made bioavailable, whether before or after absorption into the body. Examples of such suitable complexing agents include compounds containing or having added ammonium moieties.

Cationic treating agents that can be used with the invention include any agent that can form a salt or complex with anions. Nonlimiting examples of such cationic treating agents include anti-histamines, antipsychotics, antihypertensives, antiemetics, antianxiety agents, antiinfectives, pain relief agents, antidiabetic, anesthetics, anticholinergics, antihormones, or hormones. Specific examples include amitriptyline, amantadine, amiodarone, meclizine, diphenhydramine, hydroxyzine, atropine, lidocaine, benzocaine, procaine, buprenorphine, morphine, bromocriptine, bupropion, buspirone, butorphanol, chlorpromazine, clindamycin, clonidine, clomiphene, cyclobenzaprine, doxazosin, fentanyl, fluoxetine, leuprolide, octreotide, ondansetron, pioglitazone, oxybutynin, raloxifene, ticlopidine, and terbutaline.

Anionic treating agents include any agents that can form a salt or complex with cations. For anionic treating agents used with a cationic polymer, there is not typically significant hydrogen bonding, but there is still controlled, extended release. Hydrogen bonding and the associated bioadhesive properties associated therewith are, however, typically present in those embodiments of the invention wherein the anionic treating agent is complexed with a cationic complexing agent.

Nonlimiting examples of anionic treating agents useful with the present invention include naproxen, phenobarbital, foscarnet, ganciclovir, acyclovir, cidofovir, fanciclovir, penciclovir, fosinopril, divalproex, cefuroxime, pravastatin, rabeprazole, and warfarin.

In another embodiment of the invention, the compositions include a blend of both a cationic and an anionic polymer. In these embodiments the oppositely charged drugs are associated with the polymer before mixing the polymers. The invention further encompasses compositions comprising one or more treating agents. When multiple treating agents are used, the therapeutic agents can be the same or different ionic charges depending on the specific composition formulation, and the nature of the ionic polymers, used therewith.

In developing a specific formulation for treating pelvic pain, a new way to control the release of the drug was developed using the polyacrylic acid polymers, without use of an emulsion system. Not only do the polyacrylic acid polymers sustain the release, but they also control the release of drugs in our new formulations. Advantageously, there is no oil phase in these new formulations. With these new formulations, the treating agent is released over a period of at least about 6 hours, preferably at least about 12 hours, and more preferably at least about 24 hours. Typically, the treating agent is released over a period of as much as two to three days.

In one embodiment of the invention, the formulation is designed for vaginal delivery of an anti-dysrhythmic agent using polyacrylic acid polymers, such as polycarbophil, without an oil phase. In one specific example of this embodiment, as detailed below, lidocaine is the treating agent and polycarbophil is the polymer used:

| INGREDIENTS | Percent by weight |
| --- | --- |
| Lidocaine Hydrochloride USP | 6.150 |
| Purified Water USP, EP | 77.690 |
| Glycerol (Veg. Orig.) 99.5% USP, EP | 12.900 |
| NATROSOL ® 250 HHR | 2.000 |
| NOVEON ® AA1 USP | 1.000 |
| Methyl Hydroxybenzoate NF, EP | 0.180 |
| Sorbic Acid NF, EP | 0.080 |

In this embodiment of the invention some of the active ingredient, lidocaine, forms an insoluble complex with the polyacrylic acid polymer, polycarbophil, and some remains in solution in the formulation. The insoluble complex is suspended in the gel. The portion that is in solution is released immediately and the portion that has complexed with the polycarbophil is slowly released from the complex as the dissolved portion diffuses out of the formulation. Any anionic polymer would have the same role in the formulation, such as for example, Carbopol 974P. In this case, it is the polymer itself and not an emulsion system that is responsible for the controlled release of lidocaine.

Figure 1A:
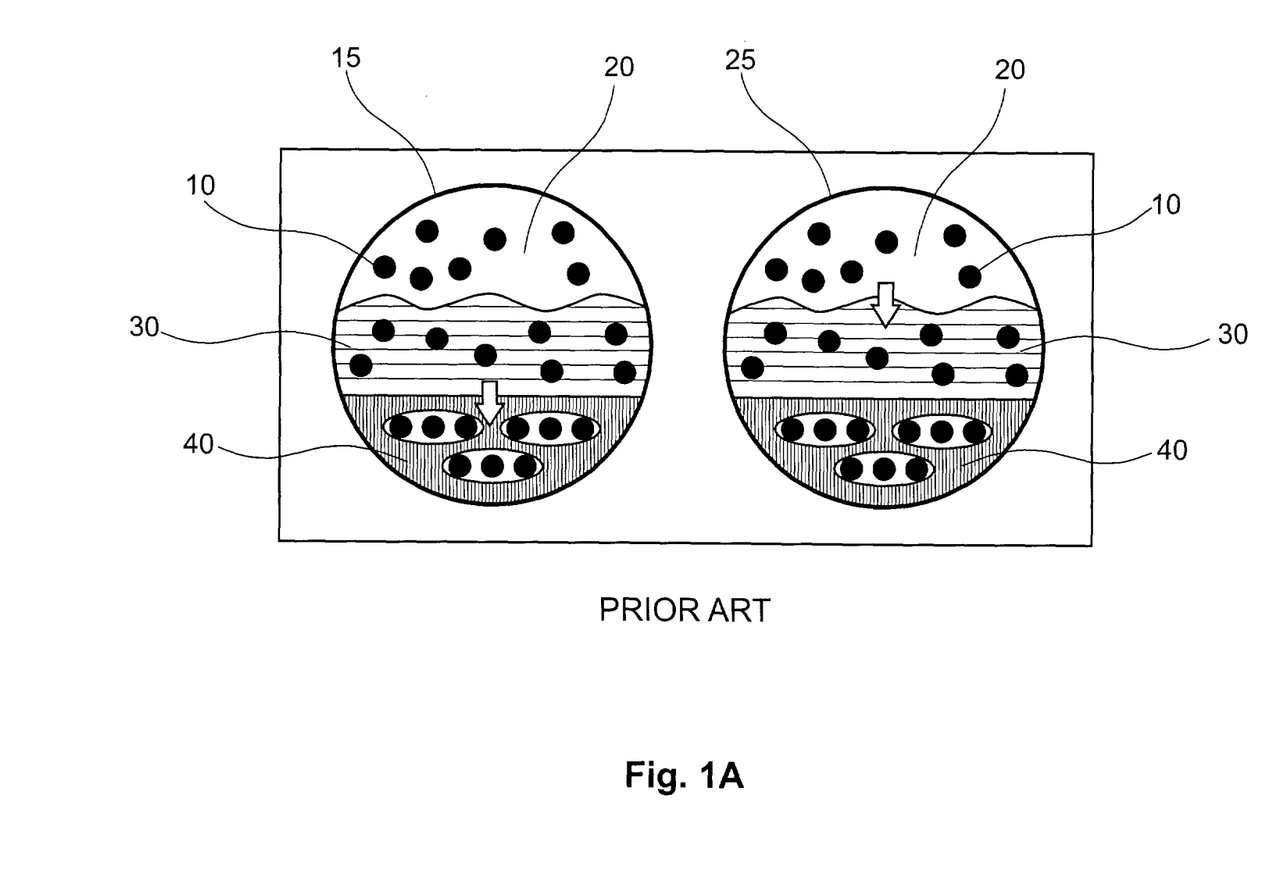
FIG. 1A shows a aqueous and oil phase polycarbophil delivery system wherein a treating agent (progesterone) diffuses to tissue from the aqueous phase and is replaced in the aqueous phase by progesterone stored in the oil reservoir ensuring a constant and controlled release of treating agent.
Figure 1B:
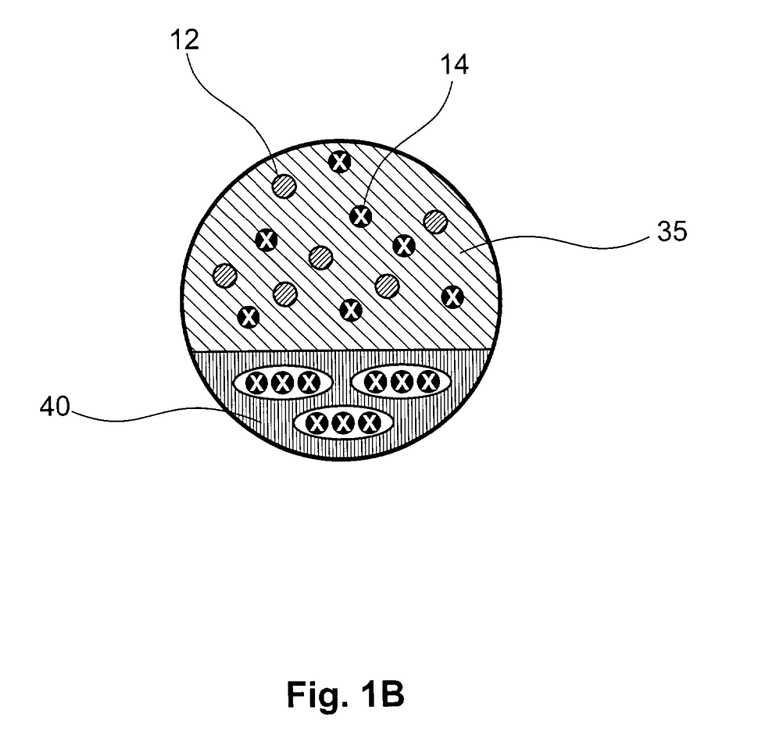
FIG. 1B shows a delivery system that is free of an oil phase having an ionic treating agent and ionic polymer wherein a portion of the treating agent is complexed with the polymer for extended delivery and the other portion of the treating agent is in solution for immediate release upon delivery.

FIGS. 1A and 1B illustrate the differences between the emulsion type delivery systems, shown in FIG. 1A, from the present oil free delivery system. The emulsion delivery system in FIG. 1A comprises a treating agent 10 dispersed in an oil phase 20 and aqueous phase 30. The treating agent 10 diffuses 15 into tissue or blood cells 40 from the aqueous phase 30. The oil phase 20 then acts as a reservoir, replacing the treating agent 10 that has diffused 15 from the aqueous phase 30, wherein the treating agent 10 from the oil phase 20 diffuses 25 into the aqueous phase 30.

In contrast to the emulsion delivery system in FIG. 1A, the present delivery system, FIG. 1B, has no oil phase. The present composition comprises an ionic polymer 35 and an ionic treating agent, wherein a portion of the treating agent 12 is chemically bound to the ionic polymer 35 and a portion of the treating agent 14 is unbound. The unbound treating agent 14 is released and absorbed by the tissue or blood cells 40 upon administration of the oil-less composition, while the bound treating agent 12 replenishes the absorbed unbound treating agent 14 in a sustained and controlled manner.

Figure 2:
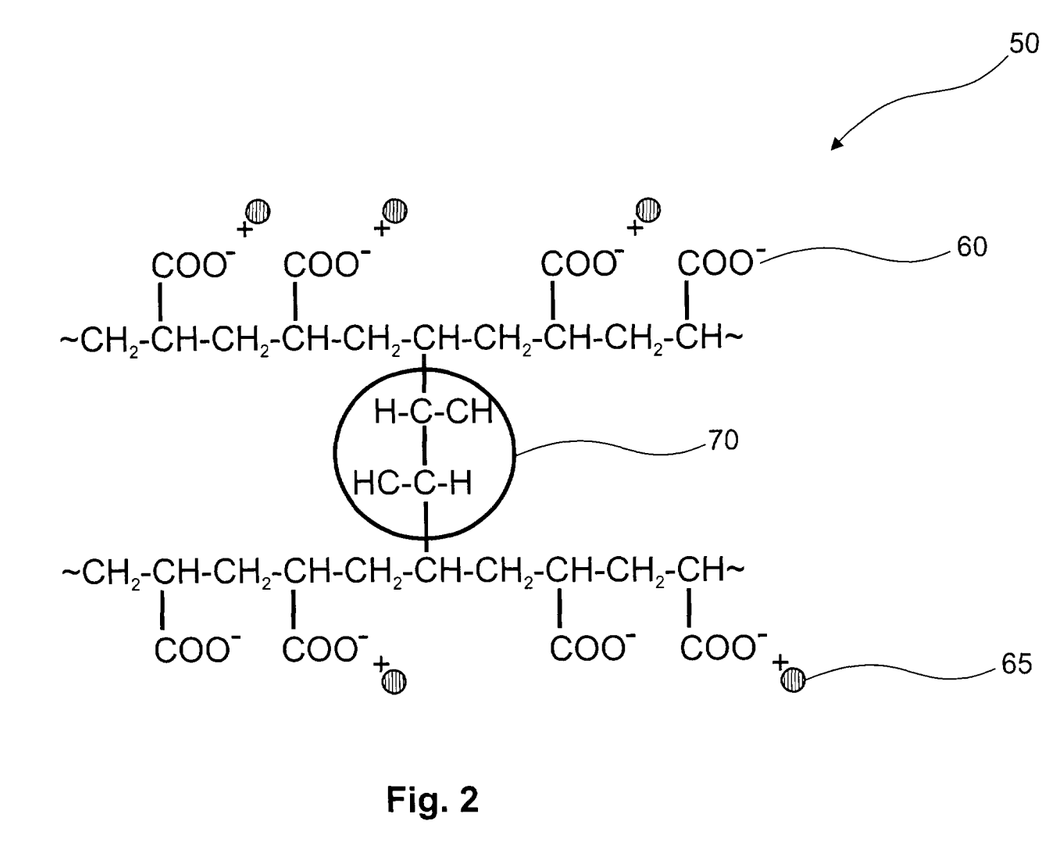
FIG. 2 shows the multiple negative charges of an anionic polymer permitting hydrogen bonding to the vaginal epithelium as well as bonding of cationic treating agents or cationic complexes.

FIG. 2 further shows a detailed representation of one embodiment of the present invention. In this embodiment the composition 50 comprises an anionic polymer 60 that chemically binds a cationic treating agent 65. The anionic polymer 60 is typically lightly cross-linked 70 and advantageously has numerous carboxyl radicals 60 for bonding the cationic treating agent 65. The composition 50 has sufficient carboxyl radicals 60 to also attach to the epithelial cells of a mucosal surface.

The present invention is applicable not only to the drugs themselves, but also to salts of the drugs. The salts are ionized upon hydration of the composition, either during the manufacturing process or upon administration to the patient.

There are several advantages of the invention include having the ability to precisely determine how much drug in the formulation will be available for immediate release and what proportion will be sustained and controlled. It is also simpler and cheaper to manufacture a gel with only an aqueous phase and no oil phase.

The present invention could be used in gel formulations prepared so that the polymer is hydrated during the manufacturing process, enabling formation of the complex between the polymer and the treating agent. As used herein, the term "gel" refers to gel-like semi-solid materials, typically having a high degree of elasticity, such as gels, jellies, pastes, creams, ointments, or similar materials.

Preparation of gel formulation typically involves hydration of the polymers by mixing the ionic polymer with water for several hours until it is fully hydrated, until a uniform, smooth, homogenous, lump-free gel-like polymer mixture is obtained. Other excipients such as, for example, sorbic acid, glycerin, and methyl paraben are typically included during mixing. When the polymers are completely hydrated, the treating agent is added and mixed in, until a homogeneous suspension is obtained.

The compositions of the present invention may also be delivered in the form of a tablet. Tablet manufacture of the invention may be accomplished according to methods known to those of ordinary skill in the art, which often involve "wet" methods of forming tablets. Determination of an appropriate manufacturing process may need to account for sensitivity of the treating agent to moisture or pH. Treating agents that are sensitive to moisture or pH means those which may be metabolized or otherwise degraded upon exposure to moisture or pH, such as may occur during the manufacturing process incorporating the agent into, for example, a gel or tablet. The time and degree of exposure to moisture or pH may affect whether and to what extent the treating agent is degraded. Accordingly, these considerations must be accounted for in the manufacturing process for a particular product.

For example, for treating agents that are not substantially sensitive to moisture, a wet granulate may be formed by mixing the treating agent with cellulose, starch, lactose, and the polymer to form a granulate. The composition is mixed until the treating agent and polymer are fully hydrated. The granulate may be dried with warm air and mixed with talc, silicon dioxide, and magnesium stearate. The mixture is then compressed to form the tablet. In a preferred embodiment for water-swellable polymers and for treating agents that are sensitive to moisture, the treating agent is added after the granulate is dried so as not to expose it to water. The polymer may also be added with the talc, silicon dioxide, and magnesium stearate after the granulate is dried. In this way, it is possible to obtain a uniform distribution of the active ingredient. The composition would then be hydrated upon administration by the user, rather than during the manufacturing process.

The invention could also be used in tablet formulations where the complex is formed when the product is used, i.e., the formulation is hydrated and the polymer-treating agent complex is formed when the product is used in the patient. Alternatively, the invention could be practiced in a tablet manufactured in a manner that hydrated the polymer, and enables the polymer-treating agent complex to form during manufacture.

In a particular embodiment of interest, as briefly discussed above, the present invention relates to a pharmaceutical composition free of an oil phase that includes an effective amount of a treating agent, intended to reduce or relieve uterine dysrhythmia by normalizing propagation of the nerve impulses and/or nerve impulses or cell to cell communication (i.e., faster, slower, or more consistent) causing the abnormal or undesirable contractions, together with a pharmaceutically acceptable bioadhesive carrier. Such anti-dysrhythmic treating agents include local anesthetics, classic "antiarrhythmics" normally associated with use for treating coronary dysrhythmias, calcium channel blockers, and autocoid agents such as prostaglandins and prostaglandin blockers, non-steroidal anti-inflammatory drugs ("NSAIDS"), COX inhibitors, thromboxane synthase inhibitors, and leukotriene inhibitors. This embodiment is also discussed in detail in U.S. application Ser. No. 10/089,796, from which much of the following discussion is taken. The following statements are exemplary of the present invention and generally only relate to this embodiment. Thus, this discussion is not meant to limit the scope of the invention generally.

Local anesthetics are generally defined as drugs that may be used to provide local numbness or pain relief, by preventing the propagation of nerve impulses that relay or report the sensation of pain. Local anesthetics useful with the instant invention may include any such anesthetic known to one of ordinary skill in the art. Lidocaine is a preferred anesthetic for use with the present invention. Other local anesthetics that may be used include cocaine, chloroprocaine, tetracaine, prilocaine, mepivacaine, buipivacaine, levobupivacaine, articaine, ropivacaine, phenol, benzocaine, pramoxine, dyclonine, etidocaine, procaine, proparacaine, dibucaine, and pramoxine.

Classic anti-arrhythmics are generally used for treating or preventing coronary arrhythmias. Such treating agents include, for example, lidocaine, phenytoin, mexiletine, tocainide, procainamide, quinidine, disopyramide, moricizine, propafenone, flecainide, sotalol, bretyllium, amiodarone, verapamil, diltiazem, digoxin, digitoxin, adenosine, propranolol, esmolol, and N-acetyl procainamide.

Calcium channel blockers are used as coronary anti-arrhythmic agents due to their actions on SA and AV nodes. These agents tend also to decrease coronary vascular resistance and increase coronary blood flow. Examples of calcium channel blockers include, without limitation, amlodipine, bepridil, diltiazem, felodipine, isradipine, nicardipine, nifedipine, nimodipine, and verapamil. The most common side effects tend to be caused by excessive vasodilation, and may cause dizziness, hypotension, headache, digital dysesthesia, and nausea. Other side effects include constipation, aggrevation of myocardial ischemia, and peripheral or pulmonary edema.

Prostaglandins and related compounds are called eicosanoids, because of their common structural derivation. Eicosanoids also include leukotrienes and thromboxane $A_2$. Prostaglandins often are potent vasodilators and/or vasoconstrictors. Certain prostaglandins reduce systemic blood pressure and increase blood flow to most organs, while others generally increase cardiac output. Leukotrienes tend to reduce coronary blood flow and thromboxane $A_2$ is a potent vasoconstrictor.

Inhibitors of eicosanoids or eicosanoid biosynthesis include prostaglandin blockers, thromboxane synthase inhibitors, leukotriene inhibitors, NSAIDS (Non-Steroidal Anti-Inflammatory Drugs), and COX inhibitors. Blocking or interfering with biosynthesis or bioactivity of various eicosanoids or eicosanoid precursors may also increase or decrease the number of contractions, not affecting the rhythm. This may occur through an indirect mechanism by affecting a peripheral or preliminary activity or synthesis.

Thromboxane synthase inhibitors include, for example, pirmagrel and dazoxiben.

Leukotriene inhibitors include, for example, zileuton.

NSAIDS include, for example, diclofenac, etodolac, fenoprofen, lurbiprofen, ibuprofen, indomethacin, ketoprofen, ketorolac, meclofenamate, fenamic acid, meloxicam, nabumetone, naproxin, oxaprozin, piroxicam, sulindac, and tolmetin.

COX inhibitors include, for example, aspirin, celecoxib, rofecoxib, and valdecoxib.

The bioadhesive carrier includes a bioadhesive, water-swellable, water-insoluble, cross-linked polycarboxylic polymer. A preferred carrier, which may be in a gel formulation, contains a polycarbophil base designed to give controlled, extended release of the local anesthetic through the vaginal mucosa. Similar formulations for administration of different treating agents for other purposes are described in U.S. Pat. Nos. 5,543,150 and 6,126,959, the contents of which are each expressly incorporated herein by reference.

U.S. Pat. No. 5,543,150 discloses and claims use of similar extended-release vaginal formulations with progesterone to provide a FIRST UTERINE PASS EFFECT: directed, local delivery of the progesterone to effect secretory transformation of the endometrium while maintaining very low blood serum levels of progesterone. Similarly, U.S. Pat. No. 6,126,959 discloses and claims use and composition of other similar extended release formulations for vaginal delivery of treating agents to effect local efficacy without also causing detrimental blood levels of the treating agent.

The invention also relates to a method for treating or preventing pelvic pain that includes administering the composition vaginally. Such administration demonstrates a therapeutic benefit for treating or preventing pelvic pain associated with uterine dysrhythmia.

The invention also relates to a method for treating or improving infertility that includes administering the composition vaginally. Such administration demonstrates a therapeutic benefit for treating or improving infertility associated with uterine dysrhythmia.

Preferably, in this embodiment, the composition is administered in dosages that contain about 0.1% to 12.5% concentrations of the treating agent depending on the treating agent used. For example, lidocaine may be administered as the treating agent in dosage concentrations of 2%, 5%, and 10%, while terbutaline is typically administered in dosage concentrations of 0.1% to 1%.

The composition of the invention is advantageously delivered to a mucosal surface, such as the vaginal, buccal, rectal, occular, or other surfaces. The composition may be applied vaginally, and may be formulated as any appropriate vaginal composition, such as, without limitation, a gel or cream, or even as a gelifying tablet for administration. When administered, the composition diffuses through the vaginal mucosal into the target tissue. Relief from pain is provided by treatment or prevention of the cause or source of the pain, e.g., increased or dysrhythmic contractility.

The treating agents in the instant compositions of this embodiment of the invention diffuse in high concentrations into the myometrium to alter dysfunctional uterine contractility for control of pain associated therewith. Systemic circulation of the treating agent remains at a low level, enabling the treatment to avoid adverse systemic side effects. Depending on both the treating agent and the formulation, which can be modified to extend or shorted the duration of release of the treating agent, the release and efficacy of the treating agent may easily last for at least about 48 hours or more.

A preferred local anesthetic for use with the present invention is lidocaine. Lidocaine is an antidysrhythmic agent—as are most local anesthetics. Its chemical formula is 2-(diethylamino)-N-(2,6-dimethylphenyl) acetamide. Its molecular weight is 234.34. Its structural formula is:

Lidocaine is an extremely safe, effective anesthetic when it is delivered locally to the site of action—though significant blood serum levels of lidocaine may also cause adverse side effects. It has a half-life of about 1.5 to 2 hours, which is sufficiently long to make it practical to use in sustained release formulations.

The specific drug delivery formulation chosen may include a cross-linked polycarboxylic acid polymer formulation, generally described in U.S. Pat. No. 4,615,697 ("the '697 patent"), the content of which is expressly incorporated herein by reference thereto. In general, at least about 80% of the monomers of the polymer in such a formulation should contain at least one carboxyl functionality. The cross-linking agent should be present at such an amount as to provide enough bioadhesion to allow the system to remain attached to the target epithelial surfaces for a sufficient time to allow the desired dosing to take place. Of course, higher doses can be formulated readily by one of skill in the art to be released more slowly over a longer period of time; the key factor is the amount of treating agent administered per unit time, while the concentration of the formulation can be varied inversely with the amount of formulation per unit dosage, or varied directly with the duration of release of the treating agent. In other words, a higher concentration of treating agent in the formulation can be delivered more slowly, and/or in a smaller dose of the formulation, to achieve the same overall rate of delivery of the treating agent.

For vaginal administration of this embodiment of the invention, the formulation preferably remains attached to the epithelial surfaces for a period of about 24 to 48 hours. Such results may be measured clinically over various periods of time, by testing samples from the vagina for pH reduction due to the continued presence of the polymer. This level of bioadhesion is generally attained when the cross-linking agent is present at about 0.1 to 6 weight percent of the polymer, preferably about 1 to 2 weight percent. Bioadhesion can also be measured using commercially available surface tensiometers utilized to measure adhesive strength.

The polymer formulation can be adjusted to control the release rate of the local anesthetic, such as lidocaine, by varying the amount of cross-linking agent in the polymer. Suitable cross-linking agents include divinyl glycol, divinylbenzene, N,N-diallylacrylamide, 3,4-dihydroxy-1,5-hexadiene, 2,5-dimethyl-1,5-hexadiene, and similar agents.

A preferred polymer for use in such a formulation is Polycarbophil, U.S.P., which is commercially available from Noveon, Inc., of Cleveland, Ohio under the trade name NOVEON®-AA1. Polycarbophil is a polyacrylic acid cross-linked with divinyl glycol.

Other useful bioadhesive polymers that may be used in such a drug delivery system formulation are mentioned in the '697 patent. For example, these include polyacrylic acid polymers cross-linked with 3,4-dihydroxy-1,5-hexadiene, and polymethacrylic acid polymers cross-linked with divinyl benzene.

Typically, these polymers would not be used in their salt form, because this would decrease their bioadhesive capability and also inhibit binding of ionic drugs. Divalent salts, such as calcium salts, cause the greatest decrease in bioadhesion. Monovalent salts, such as sodium salts, typically do not reduce bioadhesion as much.

Such bioadhesive polymers may be prepared by conventional free radical polymerization techniques utilizing initiators such as benzoyl peroxide, azobisisobutyronitrile, and the like. Exemplary preparations of useful bioadhesives are provided in the '697 patent.

The bioadhesive formulation may be in the form of a gel, cream, tablet, pill, capsule, suppository, film, or any other pharmaceutically acceptable form that adheres to the mucosa and does not wash away easily. The preferred formulation for the present invention is in the form of a gel.

Additionally, the additives taught in the '697 patent may be mixed in with the cross-linked polymer in the formulation for maximum desired efficacy of the delivery system or for the comfort of the patient. Such additives include, without limitation, one or more of the following: lubricants, plasticizing agents, preservatives, gel formers, tablet formers, pill formers, suppository formers, film formers, cream formers, disintegrating agents, coatings, binders, vehicles, coloring agents, odor controlling agents, humectants, viscosity controlling agents, pH-adjusting agents, and other similar, commonly-used agents.

This embodiment of the present composition may be delivered to the vagina in a variety of fashions as known in the art, such as (without limitation) plunger, douche, and manually. One method of delivery is to use a device similar to those described in U.S. Design Pat. Nos. D345,211 and D375,352. These devices are oblong hollow tube containers, with one end capable of being opened and the other end containing most of the composition to be delivered in a sealed container that may be used relatively easily by the patient. Said containers also maintain the formulation and treating agent in a sealed, sterile environment until use. Upon use, such a container is opened and the open end is inserted into the vagina, while the other end is squeezed to deliver the contents of the container into the vagina.

This embodiment of the present invention thus may be used to treat the underlying cause of the pain by delivering sufficient quantity of the treating agent to the affected tissue for an extended period of time. The delivery system provides a constant source of the drug which achieves concentrations that affect contractility of the tissue, while keeping systemic concentrations low enough to avoid adverse effects.

EXAMPLES

The following exemplary formulations may be made according to the present invention. They are also present in U.S. application Ser. No. 10/089,796. All ingredients are listed in percentage by weight.

|  | Ex. 1 | Ex. 2 | Ex. 3 | Ex. 4 | Ex. 5 | Ex. 6 | Ex. 7 | Ex. 8 | Ex. 9 | Ex. 10 | Ex. 11 |
|---|---|---|---|---|---|---|---|---|---|---|---|
| Lidocaine Hydrocloride USP | 6.15 | 6.15 | 6.15 | 6.15 | 6.15 | 6.15 | 12.30 | 12.30 | 12.30 | 2.46 | 2.46 |
| Polycarbophil USP | 1.00 | 0.75 | 1.25 | 1.50 | 1.00 | 0.75 | 1.00 | 1.00 | 1.00 | 1.00 | 0.75 |
| Carbopol 974P NF |  |  |  |  |  |  | — | 1.00 | 1.50 | — | — |
| NATROSOL ® 250 HHX | 2.00 | 2.25 | 1.50 | 1.50 | 2.00 | 2.00 | 2.00 | 1.00 | — | 2.00 | 2.00 |
| Glycerol USP/BP | 12.90 | 12.90 | 12.90 | 12.90 | 15.00 | 12.90 | 12.90 | 12.90 | 12.90 | 12.90 | 12.90 |
| Sorbic acid NF/EP | 0.08 | 0.08 | 0.08 | 0.08 | 0.08 | 0.08 | 0.80 | 0.80 | 0.80 | 0.80 | 0.80 |
| Methyl Hydroxybenzoate NF, EP | 0.18 | 0.18 | 0.18 | 0.18 | 0.18 | 0.18 | 0.18 | 0.18 | 0.18 | 0.18 | 0.18 |
| Purified water USP/EP | 77.69 | 77.69 | 77.94 | 77.69 | 75.59 | 77.94 | 70.82 | 70.82 | 71.32 | 80.66 | 80.91 |

|  | Ex. 12 | Ex. 13 | Ex. 14 | Ex. 15 | Ex. 16 | Ex. 17 | Ex. 18 | Ex. 19 | Ex. 20 | Ex. 21 | Ex. 22 |
|---|---|---|---|---|---|---|---|---|---|---|---|
| Ibuprofen | 2.50 | 2.50 | 2.50 | 2.50 | 2.50 | 2.50 | 5.00 | 5.00 | 5.00 | 1.25 | 1.25 |
| Polycarbophil USP | 1.00 | 0.75 | 1.25 | 1.50 | 1.00 | 0.75 | 1.00 | 1.00 | 1.00 | 1.00 | 0.75 |
| Carbopol 974P NF |  |  |  |  |  |  | — | 1.00 | 1.50 | — | — |
| NATROSOL ® 250 HHX | 2.00 | 2.25 | 1.50 | 1.50 | 2.00 | 2.00 | 2.00 | 1.00 | — | 2.00 | 2.00 |
| Glycerol USP/BP | 12.90 | 12.90 | 12.90 | 12.90 | 15.00 | 12.90 | 12.90 | 12.90 | 12.90 | 12.90 | 12.90 |
| Sorbic acid NF/EP | 0.08 | 0.08 | 0.08 | 0.08 | 0.08 | 0.08 | 0.80 | 0.80 | 0.80 | 0.80 | 0.80 |
| Methyl Hydroxybenzoate NF, EP | 0.18 | 0.18 | 0.18 | 0.18 | 0.18 | 0.18 | 0.18 | 0.18 | 0.18 | 0.18 | 0.18 |
| Purified water USP/EP | 81.34 | 81.34 | 81.59 | 81.34 | 79.24 | 81.59 | 78.12 | 78.12 | 78.62 | 81.87 | 82.12 |

|  | Ex. 23 | Ex. 24 | Ex. 25 | Ex. 26 | Ex. 27 | Ex. 28 | Ex. 29 | Ex. 30 | Ex. 31 | Ex. 32 | Ex. 33 |
|---|---|---|---|---|---|---|---|---|---|---|---|
| Diltiazem | 2.50 | 2.50 | 2.50 | 2.50 | 2.50 | 2.50 | 3.50 | 3.50 | 3.50 | 1.25 | 1.25 |
| Polycarbophil USP | 1.00 | 0.75 | 1.25 | 1.50 | 1.00 | 0.75 | 1.00 | 1.00 | 1.00 | 1.00 | 0.75 |
| Carbopol 974P NF |  |  |  |  |  |  | — | 1.00 | 1.50 | — | — |
| NATROSOL ® 250 HHX | 2.00 | 2.25 | 1.50 | 1.50 | 2.00 | 2.00 | 2.00 | 1.00 | — | 2.00 | 2.00 |
| Glycerol USP/BP | 12.90 | 12.90 | 12.90 | 12.90 | 15.00 | 12.90 | 12.90 | 12.90 | 12.90 | 12.90 | 12.90 |
| Sorbic acid NF/EP | 0.08 | 0.08 | 0.08 | 0.08 | 0.08 | 0.08 | 0.80 | 0.80 | 0.80 | 0.80 | 0.80 |
| Methyl Hydroxybenzoate NF, EP | 0.18 | 0.18 | 0.18 | 0.18 | 0.18 | 0.18 | 0.18 | 0.18 | 0.18 | 0.18 | 0.18 |
| Purified water USP/EP | 81.34 | 81.34 | 81.59 | 81.34 | 79.24 | 81.59 | 79.62 | 79.62 | 80.12 | 81.87 | 82.12 |

The local anesthetic will generally be used in its basic or unprotonated form. In this form, the anesthetics are only slightly soluble in water. In another form, the anesthetics may be used as water-soluble salts, such as hydrochlorides. The unprotonated form of the anesthetic is necessary for diffusion through cellular membranes to reach the site of action. Cationic species interact preferentially with the $Na^+$ channels. In a preferred embodiment, the anesthetic is used in its basic form and is suspended in a gel or gelifying tablet for delivery.

Local anesthetics, such as lidocaine, act on the uterine muscle as an antiarrhythmic and reverse uterine dyskinesia as a means of preventing pain of uterine cramping associated with dyskinesia rather than frequency of contractions. The anesthetics also prevent endometriosis by limiting retrograde menses caused by dysrhythmic contractions, and may also aid sperm transport in women with infertility linked to mild endometriosis associated with dysmenorrhea.

Typical oral or injection forms of anesthetics would need to achieve high blood levels in order to reach uterine tissue levels sufficient to demonstrate anti-dysrhythmic efficacy. Even so-called "trigger-point" injections would tend to cause higher blood levels, and present distinct disadvantages with regard to convenience and comfort of administration when compared to the instant formulations.

| Terbutaline sulfate | 0.40% |
|---|---|
| Carbopol 974P | 3.00% |
| Polycarbophil | 2.00% |
| Glycerin | 12.90% |
| Methyl paraben | 0.18% |
| Sorbic Acid | 0.08% |
| Water | 81.44% |

A nonlimiting example of a suitable formulation for vaginal delivery of anti-dysrhythmics comprises polycarbophil, carbopol, NATROSOL® 250HHX, glycerol, sorbic acid, methyl hydroxybenzoate, and purified water mixed with an anti-dysrhythmic, preferably lidocaine or ibuprofen.

Sorbic acid and methylhydroxybenzoate are preservatives, which may be substituted by other known preservatives, such as benzoic acid, propylparaben, or propionic acid.

Carbopol® is a gel former, preferably Carbopol® 974P, but may be substituted by other gel formers including, but not limited to Carbopol® 934P, Carbopol® 940, or Carbopol® 980. In fact, any carbomer known to those of ordinary skill in the art as forming a gel could be used with the invention.

NATROSOL® 250 HHX is a viscosity-enhancing agent, but may be substituted by other viscosity-enhancing agents, such as methyl cellulose or propyl cellulose.

Glycerol is a humectant; alternative humectants include, for example, propylene glycol and dipropylene glycol.

As will be apparent to those skilled in the art, the composition can be varied to affect certain properties. For example, the concentration of the bioadhesive polymer can be adjusted to provide greater or lesser bioadhesion. The viscosity can be varied by varying the pH or by changing the concentration of the polymer or gel former. The pH also can be varied as appropriate to affect the release rate or bioadhesiveness of the formulation. All ingredients are well known and readily available from supplier known in the industry.

Thus, in this embodiment, the present invention provides uses and compositions for vaginal administration of anti-dysrhythmic agents to treat pelvic pain associated with dysrhythmia. The extended-release formulations enable effective local treatment without also causing blood levels sufficient to induce adverse side effects.

Any and all publications and patent applications mentioned in this specification are indicative of the level of skill of those skilled in the art to which this invention pertains. All publications and patent applications mentioned herein are hereby incorporated by reference to the same extent as if each individual publication or application was specifically and individually incorporated by reference.

It is to be understood that the invention is not to be limited to the exact configuration as illustrated and described herein. Accordingly, all expedient modifications readily attainable by one of ordinary skill in the art from the disclosure set forth herein, or by routine experimentation therefrom, are deemed to be within the spirit and scope of the invention as defined by the appended claims.

What is claimed is:

1. A bioadhesive pharmaceutical composition comprising an ionic treating agent and an ionic polymer, wherein the composition is free of an oil phase; the polymer is sufficiently ionized to provide bonding with the treating agent to release the treating agent in a controlled manner over an extended period of time; and the composition is in the form of a gel at the time of administration.

2. The composition of claim 1, wherein the polymer is anionic.

3. The composition of claim 1, wherein the polymer is cationic, and the composition further includes a bioadhesive agent.

4. The composition of claim 2, wherein the treating agent is anionic, and the composition further comprises a cationic complexing agent that forms a complex with the treating agent, which complex bonds to the anionic polymer.

5. The composition of claim 4, wherein the polymer is sufficiently ionized to bond with the treating agent complex as well as to provide bioadhesion of the composition.

6. The composition of claim 2, wherein the polymer is sufficiently ionized to provide bioadhesion.

7. The composition of claim 6, wherein the polymer is a bioadhesive, water swellable, but water-insoluble cross-linked polycarboxylic acid polymer.

8. The composition of claim 7, wherein the polymer comprises polycarbophil.

9. The composition of claim 1, wherein the treating agent is released over a period of at least about 6 hours.

10. The composition of claim 2, wherein the treating agent is released over a period of at least about 12 hours.

11. The composition of claim 7, wherein the treating agent is released over a period of at least about 24 hours.

12. The composition of claim 11, wherein the treating agent is released over a period of two to three days.

13. The composition of claim 12, where the treating agent is released over a period of about 3.5 days.

14. The composition of claim 1, wherein the treating agent is a cationic treating agent.

15. The composition of claim 14, wherein the treating agent includes one or more of amitriptyline, amantadine, amiodarone, meclizine, diphenhydramine, hydroxyzine, or atropine.

16. The composition of claim 14, wherein the treating agent includes one or more of lidocaine, benzocaine, procaine, buprenorphine, morphine, bromocriptine, bupropion, buspirone, butorphanol, chlorpromazine, clindamycin, clonidine, or clomiphene.

17. The composition of claim 14, wherein the treating agent includes one or more of cyclobenzaprine, doxazosin, fentanyl, fluoxetine, leuprolide, octreotide, ondansetron, pioglitazone, oxybutynin, raloxifene, ticlopidine, or terbutaline.

18. The composition of claim 3, wherein the treating agent is an anionic treating agent.

19. The composition of claim 18, wherein the treating agent includes one or more of naproxen, phenobarbital, foscarnet, ganciclovir, acyclorvir, cidofovir, fanciclovir, penciclovir, fosinopril, divalproex, cefuroxime, pravastatin, rabeprazole, or warfarin.

20. A pharmaceutical composition comprising a treating agent and a bioadhesive, water swellable, but water-insoluble cross-linked polycarboxylic acid polymer, wherein the composition is free of an oil phase and is in the form of a gel at the time of administration, and the treating agent comprises one or more of amitriptyline, amantadine, amiodarone, meclizine, diphenhydramine, hydroxyzine, atropine, lidocaine, benzocaine, procaine, buprenorphine, morphine, bromocriptine, bupropion, buspirone, butorphanol, chlorpromazine, clindamycin, clonidine, clomiphene, cyclobenzaprine, doxazosin, fentanyl, fluoxetine, leuprolide, octreotide, ondansetron, pioglitazone, oxybutynin, raloxifene, ticlopidine, or terbutaline and is released in a controlled manner over an extended period of time.

21. The composition of claim 20, wherein the polymer comprises polycarbophil.

22. A pharmaceutical composition comprising a treating agent and a bioadhesive, water swellable, but water-insoluble cross-linked polycarboxylic acid polymer, wherein the composition is free of an oil phase and is in the form of a gel at the time of administration, and the treating agent comprises one or more of naproxen, phenobarbital, foscarnet, ganciclovir, acyclorvir, cidofovir, fanciclovir, penciclovir, fosinopril, divalproex, cefuroxime, pravastatin, rabeprazole, or warfarin and is released in a controlled manner over an extended period of time.

23. The composition of claim 22, wherein the polymer comprises polycarbophil.

24. A pharmaceutical composition for treating or preventing pelvic pain, or for treating or improving infertility, associated with uterine dysrhythmia comprising a therapeutically effective amount of an ionic, anti-dysrhythmic treating agent and a bioadhesive, water swellable, but water-insoluble cross-linked polycarboxylic acid polymer, wherein the composition is free of an oil phase and is in the form of a gel at the time of administration, and the treating agent is released in a controlled manner over an extended period of time.

25. The composition of claim 24, wherein the polymer comprises polycarbophil and the treating agent is lidocaine.

26. A method of treating a disease or condition in a patient in need thereof comprising administering a composition in the form of a gel that comprises a therapeutically effective amount of an ionic treating agent and an ionic polymer; wherein the polymer is sufficiently ionized to provide bonding with the treating agent; wherein the composition is free of an oil phase and is in the form of a gel at the time of administration; and the treating agent is released in a controlled manner over an extended period of time through chemical bonding with the polymer.

27. The method claim 26, wherein the polymer is anionic, and the composition further comprises a cationic complexing agent that forms a complex with the treating agent and bonds also to the anionic polymer.

28. The method of claim 27, wherein the treating agent is released over a period of at least about 6 hours.

29. The method of claim 27, wherein the treating agent includes one or more of amitriptyline, amantadine, amiodarone, meclizine, diphenhydramine, hydroxyzine, atropine, lidocaine, benzocaine, procaine, buprenorphine, morphine, bromocriptine, bupropion, buspirone, butorphanol, chlorpromazine, clindamycin, clonidine, clomiphene, or cyclobenzaprine, doxazosin, fentanyl, fluoxetine, leuprolide, octreotide, ondansetron, pioglitazone, oxybutynin, raloxifene, ticlopidine, or terbutaline.

30. The method of claim 26, wherein the polymer is cationic and the composition further comprises a bioadhesive agent.

31. The method of claim 30, wherein the treating agent includes one or more of naproxen, phenobarbital, foscarnet, ganciclovir, acyclorvir, cidofovir, fanciclovir, penciclovir, fosinopril, divalproex, cefuroxime, pravastatin, rabeprazole, or warfarin.

32. A method of treating pelvic pain, or for treating or improving infertility, associated with uterine dysrhythmia comprising vaginally administering a composition that comprises a therapeutically effective amount of an ionic, anti-dysrhythmic treating agent and a bioadhesive, water swellable, but water-insoluble cross-linked polycarboxylic acid polymer, wherein the composition is free of an oil phase and is in the form of a gel at the time of administration, and the treating agent is released in a controlled manner over an extended period of time.

33. The method of claim 32, wherein the polymer comprises polycarbophil and the composition is formulated to release the treating agent over a period of at least two days after administration.

34. A pharmaceutical composition comprising a treating agent and a bioadhesive, water swellable, but water-insoluble cross-linked polycarboxylic acid polymer, wherein the composition is free of an oil phase and is in the form of a gel at the time of administration, and the treating agent comprises one or more agents selected from the group consisting of calcium channel blockers, autocoid agents prostaglandins, and prostaglandin blockers, non-steroidal anti-inflammatory drugs, COX inhibitors, thromboxane synthase inhibitors, and leukotriene inhibitors, wherein the treating agent is in the ionic form and is released in a controlled manner over an extended period of time.

35. The composition of claim 34, wherein the calcium channel blockers are selected from the group consisting of: amlodipine, bepridil, diltiazem, felodipine, isradipine, nicardipine, nifedipine, nimodipine, and verapamil; and the non-steroidal anti-inflammatory drugs are selected from the group consisting of: diclofenac, etodolac, fenoprofen, lurbiprofen, ibuprofen, indomethacin, ketoprofen, ketorolac, meclofenamate, fenamic acid, meloxicam, nabumetone, naproxin, oxaprozin, piroxicam, sulindac, and tolmetin.

36. The composition of claim 34, wherein the autocoid agents are selected from the group consisting of: prostaglandins and prostaglandin blockers; and the COX inhibitors are selected from the group consisting of thromboxane synthase inhibitors, and leukotriene inhibitors.

37. The composition of claim 36, wherein the thromboxane synthase inhibitors are selected from the group consisting of: pirmagrel and dazoxiben; and the leukotriene inhibitors is zileuton.

38. The method of claim 29, wherein the treating agent is terbutaline.

* * * * *

UNITED STATES PATENT AND TRADEMARK OFFICE
CERTIFICATE OF CORRECTION

PATENT NO. : 8,425,892 B2
APPLICATION NO. : 10/423920
DATED : April 23, 2013
INVENTOR(S) : William J. Bologna et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 733 days.

Signed and Sealed this
Seventh Day of October, 2014

Michelle K. Lee
*Deputy Director of the United States Patent and Trademark Office*